United States Patent [19]
Anderson et al.

[11] Patent Number: 6,055,448
[45] Date of Patent: *Apr. 25, 2000

[54] SENSOR DEVICE

[76] Inventors: John McCune Anderson, 16 Torgrange, Holywood, County Down BT18 0NG; James Allen, 10 Dunadry Road, Muckamore, County Antrim; George John Dempsey, 13 Ashley Gardens, Belfast BT15 4DN, all of United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/551,819

[22] Filed: Nov. 7, 1995

[30] Foreign Application Priority Data

Nov. 7, 1994 [IE] Ireland .................................. S940871
Jan. 30, 1995 [IE] Ireland .................................. S950070

[51] Int. Cl.⁷ ...................................................... A61B 5/04
[52] U.S. Cl. .......................... 600/372; 600/391; 600/393; 600/509
[58] Field of Search ..................................... 128/639–644, 128/702, 709; 600/372, 386–397, 509, 512

[56] References Cited

U.S. PATENT DOCUMENTS 4,121,575 10/1978 Mills et al. .
4,353,372 10/1982 Aver .
5,184,620 2/1993 Cudahy et al. .

FOREIGN PATENT DOCUMENTS 0275811 7/1988 European Pat. Off. .
3637956 7/1987 Germany .
WO90/01898 3/1990 WIPO .
WO92/07509 5/1992 WIPO .

OTHER PUBLICATIONS

Proceedings of the Annual International Conference of the IEEE Engineering in Medicine and Biology Society, Paris, France, Oct. 29–Nov. 1 1992, vol. 14, pp. 2702–2703.

Primary Examiner—Jack W. Lavinder
Assistant Examiner—David Ruddy
Attorney, Agent, or Firm—Mintz, Levin, Cohn, Ferris, Glovsky and Popeo, P.C.

[57] ABSTRACT

A sensor device for monitoring bioelectric data from the thoracic region of a human body and/or for inducing stimulating signals to said region comprises a plurality of finger-like substrate portions of a flexible dielectric material. The substrate portions are releasably attachable to the thoracic region of a human body and the lateral spacing between the substrate portions is adjustable in accordance with the physiology of the body. A plurality of electrodes are provided on each substrate portion each having a respective lead connectable to an apparatus for inducing stimulating signals to, and/or receiving physiological signals from the electrodes. Indicia or other positioning elements are provided on at least one substrate portion for indicating the correct position of the assembly in use.

18 Claims, 4 Drawing Sheets

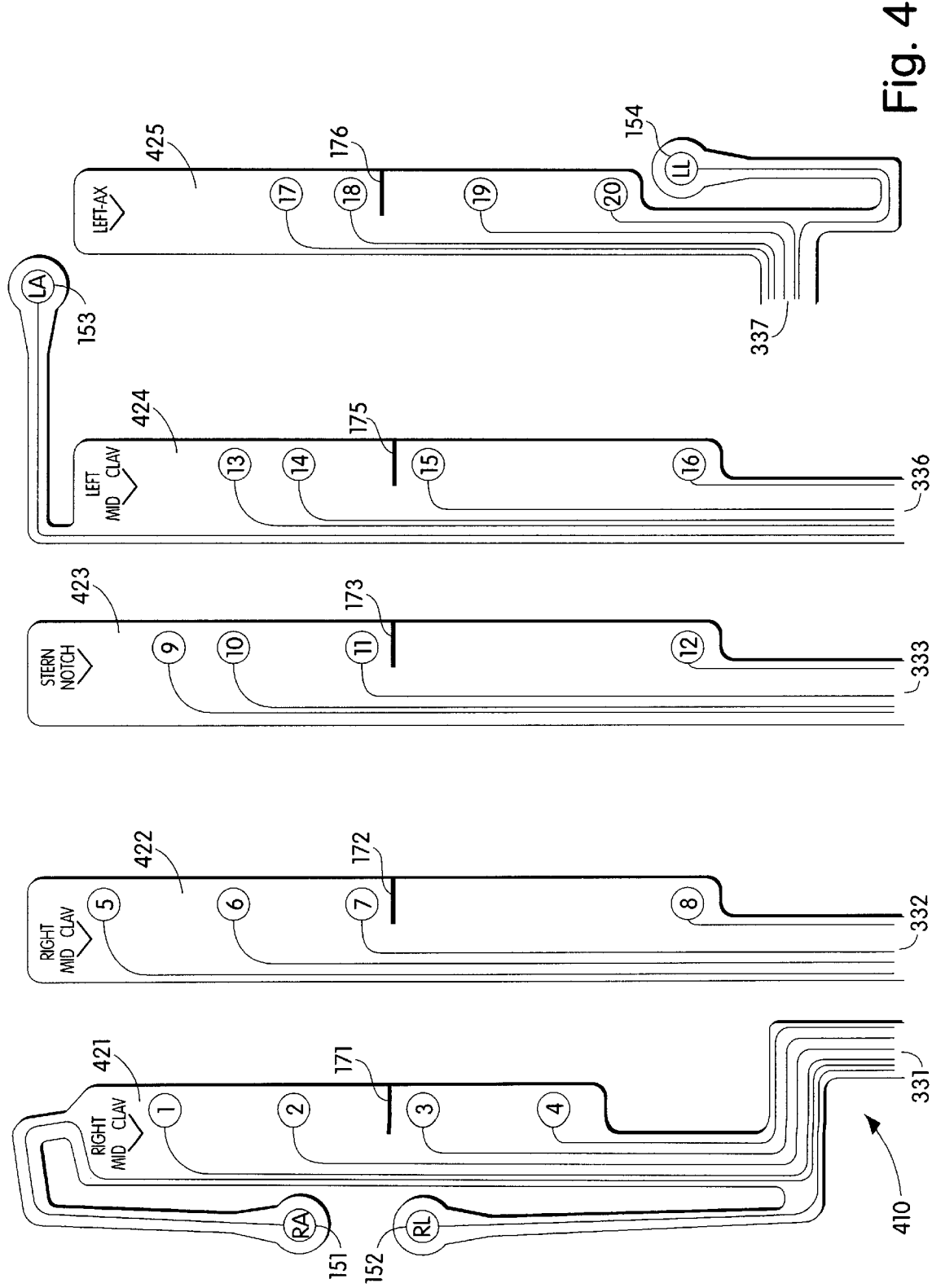

SENSOR DEVICE

FIELD OF THE INVENTION

This invention relates to a sensor device for monitoring bioelectric data from the thoracic region of a human body and/or for inducing stimulating signals to said region.

BACKGROUND TO THE INVENTION

Sensor devices are known which can monitor bioelectric data from a body. For example, B J ten Voorde in "High resolution magnetic mapping of PR-interval phenomena of normal subjects", Med. & Biol. Eng. & Comp., 26, 130–135, 1988 has reported the measurement of magnetocardiograms (MEGS) using SQUID detectors achieved by a gradiometer with fixed grid spacing of 5 cm and a total grid dimension of 25 by 30 cm. Cullen and Dempsey in "NIBEC ECG mapping harness", Proc. 14th Ann. Int. Conf. EEE Eng. in Med. & Biology Society, Pt 6, p. 2702–2703, October 1992 have reported the utilization of a fixed grid harness for body surface mapping of electrocardiograms (ECGs). Barber et al. "Extensions to the Sheffield filtered back projection algorithm to reconstruct any bipolar drive data", Proc. 15th Ann. Int. Conf. EEE Eng. in Med. & Biology Society, Pt 1, p. 78–79, 1993 have reported the use of a single row of sensor sites to perform slice imaging of applied potential tomography or electrical impedance tomography. These examples highlight some of the current techniques in obtaining body surface data. The need to extract more diagnostic information is now proving beneficial as with two dimensional and three dimensional imaging such as in X-ray and magnetic resonance imaging.

In particular, ECG body surface mapping has been shown by F. Konreich et al., "Body surface potential mapping of ST segment changes in acute myocardial infarction", Circulation, 87, 3, 1993 to improve the detection of acute myocardial infarction. This imaging modality is offering powerful means for characterizing and assessing abnormalities of myocardial muscle. In detecting acute myocardial infarction the standard 12 lead ECG which provides one of the most important first-line assessments can be often equivocal (M. Hirai et al., "Body surface isopotential maps in old anterior myocardial infarction undetectable by 12-lead electrocardiograms", American Heart Journal, Vol. 108, No. 4, Pt 1, p.975–982, 1994. Improved detection in these cases will inevitably result in benefit to the patient through quick and reliable selection of those most likely to respond to thrombolytic therapy.

One system which has reported improved sensitivity in detecting acute myocardial infarction is disclosed in British Patent Specification No. GB 2 264 176 and its counterpart U.S. Pat. No. 5,419,337, issued Jul. 14, 1995. In that specification, there is disclosed an apparatus for the detection, recording and analysis of the electrical activity of a cardiac muscle. The apparatus comprises an array of a plurality of n number of sensors where n is an integer from 40 to 100 each of which is capable of detecting an electrical signal associated with the Q and/or ST components of a heartbeat. The array is connected to a microprocessor controlled interface which in turn is connected to a microprocessor controlled analyzer and display apparatus. Each sensor provides an independent electrical picture of the heart when it is contracting as each one detects the summation of electrical changes in the heart from different angles or notional slices. Injury to the heart causes distortion or disturbance to this electrical activity and will result in changes in the potential pattern of those sensors providing information on the injured area. By means of suitable electronic systems, there is then presented a three-dimensional profile or ST map of the ST level processed from each sensor lead. The sensor array shown in the specification referred to comprises a two-dimensional array of a plurality of sensors of well-known construction.

There have been various attempts to configure sensor arrays to the thoracic surface of a human body. Dempsey et al. in "Diagnosing Myocardial Infarction using a portable Cardiac Mapping System", CEC, 2nd Eur. Conf. on Biomedical Engineering; Vol. 1, p.222–223, 1993 reported on a harness which utilizes a fixed grid array of sensors screen printed onto a flexible substrate and utilizing hydrogel sensors to enable rapid application. The Corazonix Predictor BSM-32 array marketed by Corazonix Corporation, Oklahoma, USA relies on marking the thorax into segments using a marker pen and then placing individual columns of gelled sensors into the vertical grids. Hirai et al. in "Body surface isopotential maps in old anterior myocardial infarction undetectable by 12-lead electrocardiograms", American Heart Journal, Vol. 108, No. 4, Pt 1, p. 975–982, 1984 have also reported the use of 87 sensors placed in a grated system composed of 13 columns and 7 rows on the thorax. The problem remains that to apply in excess of 20 sensors onto the thorax with anatomical consistency requires long periods of application time and is only practical under ideal clinical conditions.

SUMMARY OF THE INVENTION

It is, therefore, an object of the present invention to provide a sensor device which may be rapidly and accurately positioned on a human thorax and, in the case of repeated application to the same body, accurately at the same position each time, under a very wide range of clinical conditions regardless of body size and shape whether the body is a so-called endomorph, mesomorph or ectomorph type.

Furthermore, it is an object of the present invention to provide a sensor device which may function either as a standard 12 lead ECG type sensor array or as a sensor array for use in conjunction with, for example, the apparatus disclosed in the British Patent Specification or U.S. Patent discussed above, or which may function simultaneously as both types of sensor array.

The invention, therefore, provides a sensor device for monitoring bioelectric data from the thoracic region of a human body and/or for inducing stimulating signals to said region, the assembly comprising a plurality of finger-like substrate portions of a flexible dielectric material, the substrate portions being releasably attachable to the thoracic region of a human body and the lateral spacing between the substrate portions being adjustable in accordance with the physiology of the body, a plurality of electrodes on each substrate portion, a plurality of leads on each substrate portion each lead being connected to a respective electrode on the substrate portion, the leads being connectable to an apparatus for inducing stimulating signals to, and/or receiving physiological signals from the electrodes on the substrate portion, and positioning means on at least one substrate portion for indicating the correct position of the assembly in use.

BRIEF DESCRIPTION OF THE DRAWINGS

The invention will be understood in greater detail from the following description of preferred embodiments thereof given by way of example only and with reference to the accompanying drawings, in which:

FIG. 4 is a plan view of a fourth embodiment of an assembly according to the invention.

DESCRIPTION OF PREFERRED EMBODIMENTS

Figure 1:
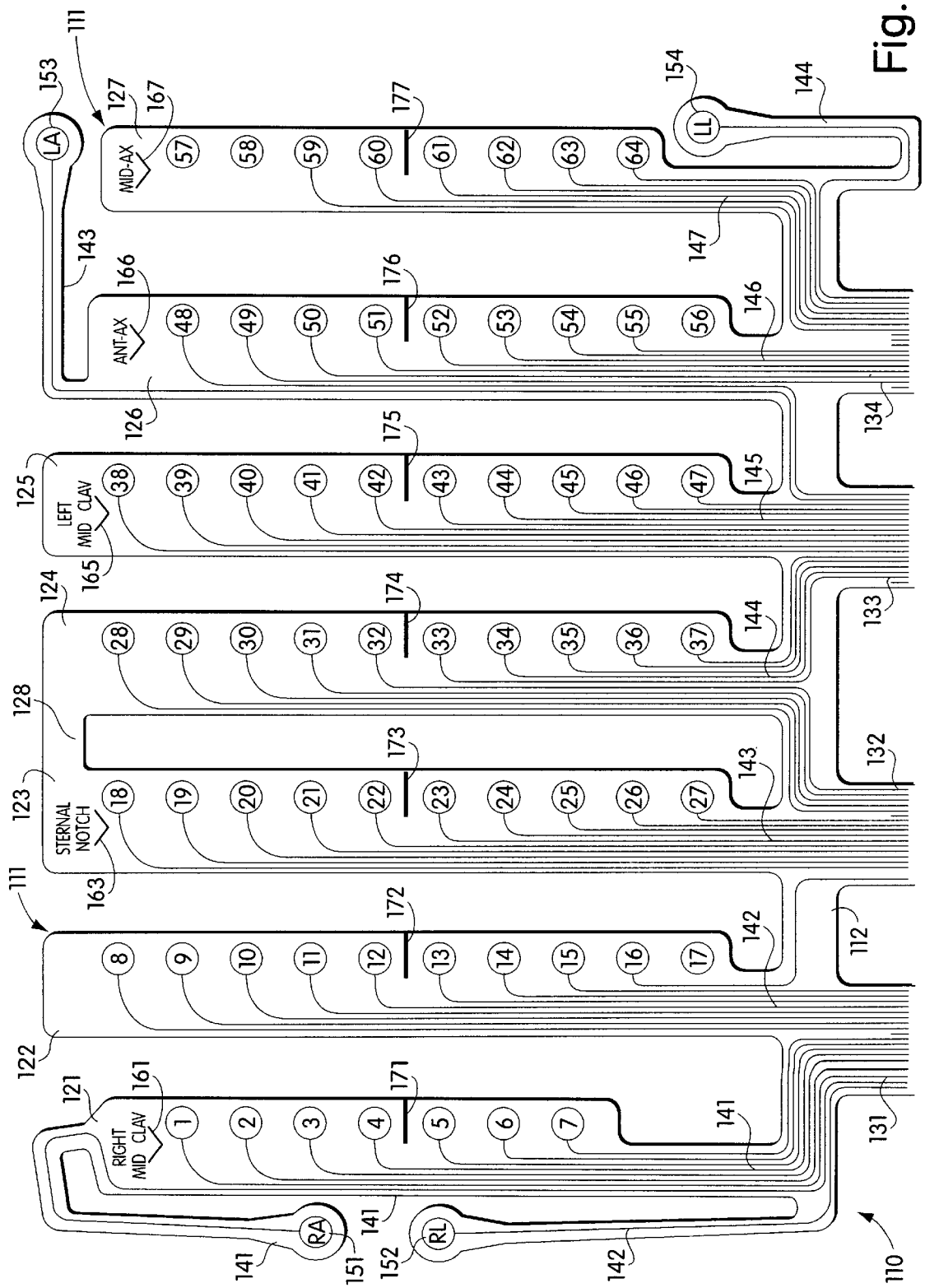
FIG. 1 is a plan view of a first embodiment of an assembly according to the invention.

FIG. 1 shows a sensor device 110 for receiving physiological signals from, or for inducing stimulating signals to, the anterior thorax region of a living human body. In particular, the physiological signals emanate from, or the inducing signals are directed to, the cardiac muscle of the body.

The sensor device 110 comprises a flexible substrate 111 of dielectric material having a plurality of electrodes or sensors thereon. In FIG. 1 each of these electrodes is numbered respectively from 1 to 64 and thus there are 64 electrodes in total. The electrodes 1–64 may be applied to the substrate 111 by well-known techniques including screen printing. Each electrode has associated therewith a respective electrical lead, which may be screen printed on the substrate at the same time as the electrode. Each electrode 1 to 64 and its associated lead is in electrical isolation from all the other electrodes and their leads.

The substrate 111 is formed with at least two finger-like projections of which, in the present embodiment, there are seven such projections 121 to 127 respectively. The projections 121–127 are substantially parallel to one another. Each of the projections 122–125 has ten electrodes thereon. Thus, the projection 122 has electrodes 8–17, the projection 123 has electrodes 18–27, the projection 124 has electrodes 28–37 and the projection 125 has electrodes 38–47. The projection 121 has seven electrodes 1–7, the projection 126 has nine electrodes 48–56 and the projection 127 has eight electrodes viz. electrodes 57–64.

There is also a common substrate portion 112 which is connected to all the projections 121–127 and which has at least one terminal portion. In the present embodiment the common substrate portion 112 has four terminal portions 131, 132, 133 and 134 each projecting from the opposite edge of the common substrate portion 112 to the projections 121–127. Each projection 121–127 has printed thereon the leads for the electrodes carried by that projection; thus the projection 121 has the leads for the electrodes 1–7, the projection 122 has the leads for the electrodes 8–17, and so on. A collection of such leads is referred to as an electrically conductive network. In the present case there are seven such networks 141–147, one for each of the projections 121–127, which eventually terminate in one or more of the terminal portions 131–134.

The substrate 111 farther comprises at least one extension. In the present embodiment there are four extensions 141–144. Each extension 141–144 has a respective electrode 151–154 screen printed thereon, and each electrode 151–154 has a respective screen printed lead which terminates in a terminal portion 131 or 134.

As will be observed from FIG. 1, each projection 121–127 has the associated plurality of electrodes arranged in columnar formation thereon. This illustrates a preferred, though not essential, feature of the invention, which is that on each projection the electrodes lie substantially along a straight line parallel to the longitudinal axis of the projection. For reasons which will become clear later in this specification, the finger-like projection 123 and 124 may be interconnected by a portion of the substrate 111 at 128.

In order to assist in the accurate and reproducible placement of the sensor device 110 on the anterior thorax region of a body, appropriate datum marks or indicia are provided. While these datum marks or indicia may be located anywhere on the device 110, it is preferable that they be located as follows. On the projection 121, an indicium 161 is shown in the form of an arrow 161. If desired, this arrow 161 may be labeled with the legend "RIGHT MID-CLAVICLE" or "RIGHT MID CLAV" to denote the precise position on the body this part of the assembly 110 should be placed. As an alternative, the arrow 161 may be labeled with a unique non-text mark or symbol and, by reference to a "key" contained within a set of instructions provided with the assembly 110, a user may determine the desired position of the arrow 161 from the associated mark or symbol. This is particularly useful where the arrow 161 and associated unique identifying mark or symbol are also screen printed simultaneously with the electrodes 1–64 and the assembly 110 is destined for use in a variety of countries with different language requirements.

Similarly, the projection 123 has an arrow 163 labeled "STERNAL NOTCH", the projection 125 has an arrow 165 labeled "LEFT MID-CLAVICLE" or "LEFT MID CLAV", the projection 124 has an arrow 164 labeled "ANTERIOR-AUXILIARY" or "ANT AUX" and the projection 127 has an arrow 167 labeled "MID-AUXILIARY" or "MID AUX". In place of the arrows 161, 163, 165, 166 and 167, there may be provided respective notches in the substrate 111 corresponding to the desired positions of the body. As before, instead of text each arrow could have a unique symbol associated therewith whose meaning is derivable from a key in the accompanying instructions.

Each of the extensions 141–144 may also bear suitable legends to represent or teach to the user that the electrode 151 is for the right arm (RA), the electrode 152 for the right leg (RL), the electrode 153 for the left arm (LA) and the electrode 154 for the left leg (LL). These legends may also be screen printed on the substrate.

Each of the projections 121–127 has a respective further indicium thereon which may also be screen printed contemporaneously with the screen printing of the electrodes 1–64. In the present example these further respective indicia are represented by respective lines (or slits) 171–177. The line 171 is located between electrodes 4 and 5, the line 172 between electrodes 12 and 13, the line 173 between electrodes 22 and 23, the line 174 between electrodes 32 and 33, the line 175 between electrodes 42 and 43, the line 176 between the electrodes 51 and 52 and the line 177 between the electrodes 60 and 61. Whereas the arrows 161, 163 and 165–167 provide for the correct placement of the sensor device 110 across the width of the thorax of the body, the lines 171–177 provide for the correct placement of the sensor device 110 relative to the height of the body.

When the arrows 161–165 are in register with the relevant portions of the body and the lines 171–177 are in substantially the same notional straight or curved line, correct placement of the sensor device 110 is achieved, in which the projections 121–127 will be in substantially parallel spaced-apart relationship. It will be appreciated that not only is correct placement achieved but also that when the sensor device 110 is placed subsequently on the same body, reproducibility of results is obtained. In other words, the same locations of the cardiac muscle are monitored. Furthermore, having regard to the ability of the projection 121–127 to be moveable relative to each other, the size of the thorax, be it on an endomorph, ectomorph or mesomorph type, is irrelevant as the arrows 161–165 may be placed on the relative anatomical locations. It will be observed that the projection 122 does not have an indicium equivalent to the indicium 161 or 163, for example. This is because in medical practice, the location of the projection 122 is not related to a precise nameable location on the body but is instead located, in use, mid-way between the projection 121 and the projection 123. The projections 123 and 124 may be joined and the desired location of the projection 124 is again located midway between projections 123 and 125 when in use.

Prior to use of the sensor device 110 and during the course of manufacture, it is preferred to provide a removable backing strip (not shown) which would provide a support for the projections 121–127 and the extensions 141–144. Thus, the assembly together with the backing strip would be of unitary construction. Further, during the course of manufacture, it is envisaged that the substrate 111 would also be of unitary construction without any separation between the projections 121–127 or extensions 141–144. Following screen printing and attachment to the backing strip (either before or after printing), the projections 121–127 and 141–144 are provided by cutting and removal of the excess substrate from the backing strip. When the backing strip is removed, the projections 121–127 and the extensions 141–144 are moveable relative to each other being connected to the common substrate portion 112. The assembly may be constructed using techniques and materials known in the art. The electrodes 1–64 and 151–154 may be pre-gelled using adhesive hydrogel.

In use of the assembly described with reference to FIG. 1, the sensor device 110 is offered to the anterior thorax of a body and the various indicia previously described are aligned and placed in the desired locations, it being appreciate that the flexible nature of the substrate and the configuration thereof as finger-like projections permits the lateral spacing between adjacent projections 121–127 to be adjusted in accordance with the physiology of the body. The terminal portions 131–134 are connected to a suitable apparatus and observations of cardiac activity may be made. The manner of releasable attachment is well-known in electrode technology and need not be described here. A suitable apparatus is that shown in British Patent Specification No. 2,264,176 or its counterpart U.S. Pat. No. 5,419,337, the disclosure of which is hereby incorporated by reference as part of the specification.

Thus, it is possible to obtain accurate and reproducible cardiac mapping techniques using the sensor device 110 and a suitable analyzer of the type disclosed in the said British Patent Specification.

The sensor device 110 may be used in a number of different modes of operation. It can be used for cardiac mapping as just described using the 64 electrodes. Additionally, the sensor device may be used in classic 12-lead ECG monitoring. In a 12-lead ECG apparatus, the leads are conventionally labeled as follows: LI, LII, LIII, aVR, aVL, aVF, V1, V2, V3, V4, V5 and V6.

Correlating these leads with all of the electrodes of the sensor device 110 produces the following result: the signal corresponding to lead LI is derived from the signals received from the electrode 151 (RA) and 153 (LA). Similarly, the signal corresponding to lead LII is derived from the electrodes 151 (RA) and 154 (LL) and the signal corresponding to lead LIII is derived from the electrodes 153 (LA) and 152 (RL).

The signal corresponding to lead aVR is given by the equation $$aVR=RA-0.5(LA+LL).$$

The signal corresponding to lead aVL is given by the equation $$aVL=LA-0.5(LL+RA).$$

The signal corresponding to lead aVF is given by the equation $$aVF=LL-0.5(LA+RA).$$

The signals corresponding to leads V1–V6 are respectively derived from electrodes 12, 22, 32, 42, 51 and 60 as follows:

$$V1=v1-(LA+RA+LL)/3$$

$$V2=v2-(LA+RA+LL)/3$$

$$V3=v3-(LA+RA+LL)/3$$

$$V4=v4-(LA+RA+LL)/3$$

$$V5=v5-(LA+RA+LL)/3$$

$$V6=v6-(LA+RA+LL)/3$$

where v1–v6 are the voltages measured at electrodes 12, 22, 32, 42, 51 and 60 respectively.

Figure 2:
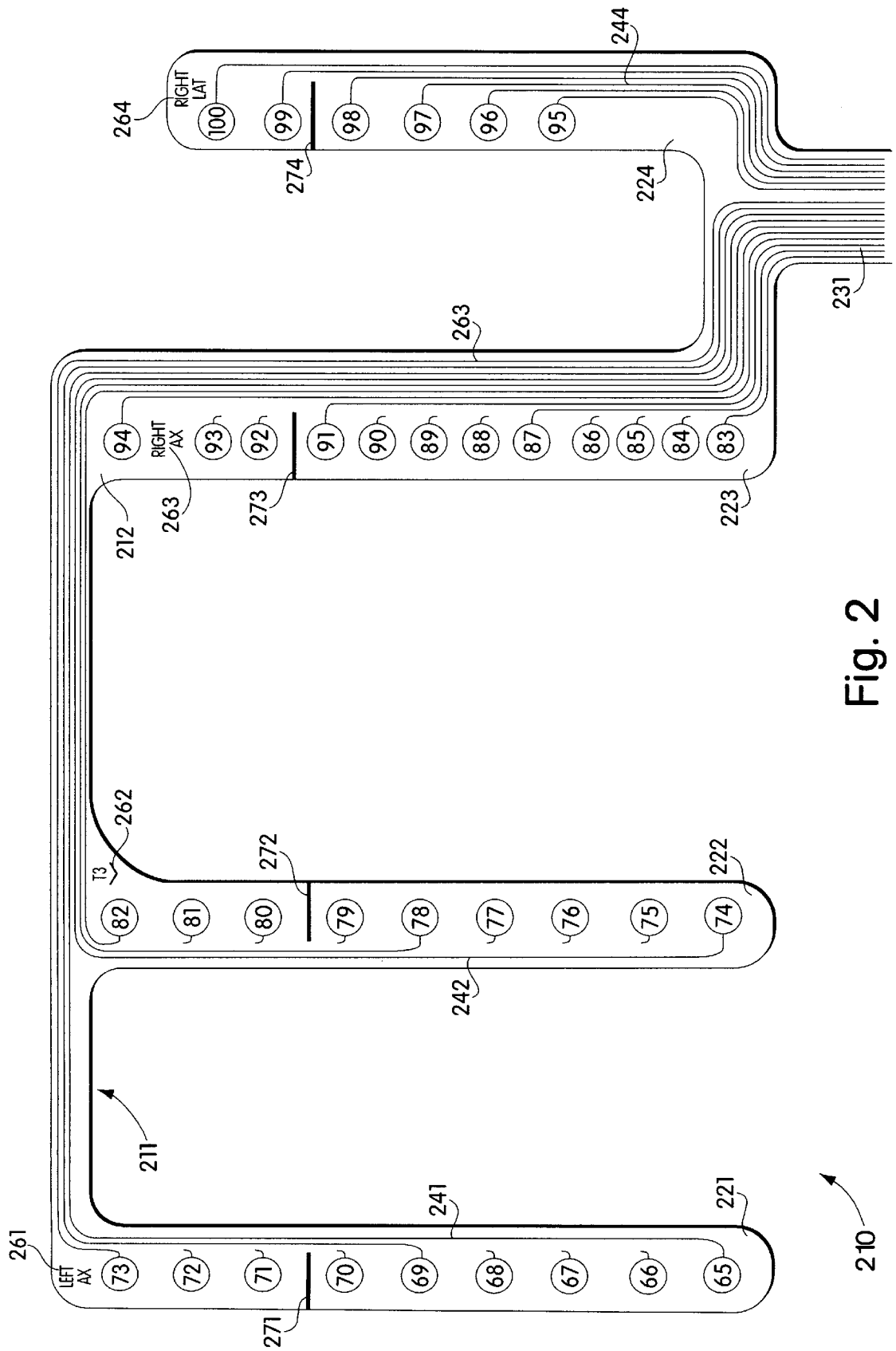
FIG. 2 is a plan view of a second embodiment of an assembly according to the invention.

Referring now to FIG. 2 of the drawings, there is shown a sensor device 210 for receiving physiological signals from, or for inducing stimulating signals to, the posterior thorax region of a human body. The sensor device 210 is similar in many respects to the device 110 and may be used in conjunction with or independently of the device 110.

Specifically, the sensor device 210 comprises a flexible substrate 211 of dielectric material having a plurality of electrodes thereon. In the drawing, each of these electrodes is numbered respectively from 65–100 inclusive and thus there are 36 electrodes in total. As in the case of the first embodiment, each electrode 65–100 has an associated lead and each electrode and lead electrically isolated from all the others. The electrodes 65–100 and associated leads may be applied to the substrate 211 by well-known techniques including screen printing.

The substrate 211 is formed with two or more finger-like projections of which, in the present embodiment, there are four such projections 221–224. The projections 221 and 222 each has nine electrodes thereon, the projection 221 having electrodes 65–73 and the projection 222 having electrodes 74–82. The projection 223 has twelve electrodes 83–94 and the projection 224 has six electrodes 95–100. The leads associated with the electrodes form electrically conductive networks 241–244 on the projections 221–224 respectively. For reasons of clarity, in the case of the projections 221, 222 and 223, the conductive networks 241, 242 and 243 are shown without all leads present. In practice, each electrode 65–94 would have a respective lead as shown in the case of the projection 224. The substrate 211 has a projecting terminal portion 231 at which the four networks 241–244 eventually terminate. As before, on each projection 221–224 the electrodes preferably lie substantially along a straight line parallel to the longitudinal axis of the projection.

In order to assist in the accurate and reproducible placement of the sensor device 210 on the posterior thorax region of a body, appropriate datum marks or indicia are provided. As an alternative to indicia, notches, openings, slits or other similar techniques may be used for enabling accurate and reproducible placement of the assembly 210. While these datum marks or indicia may be located anywhere on the device 210, it is preferable that they be located as follows. On the projection 222 an indicium 262 is shown in the form of an arrow 262. If desired, this arrow 262 may be labeled with the legend "T3" to denote the precise position on the body this part of the sensor device should be placed. As an alternative, the arrow 262 may be labeled with a unique non-text mark or symbol and, by reference to a "key" contained within a set of instructions provided with the device 210, a user may determine the desired position of the arrow 262 from the associated mark or symbol.

Similarly. the projection 221 may be labeled in the manner previously described with the legend "LEFT AX", 261, the projection 223 may be labeled "RIGHT AX", 263, and the projection 224 may be labeled "RIGHT LAT", 264. In place of the arrow/legends 261–264 there may be provided respective notches in the substrate 211 corresponding to the desired positions of the body.

Each of the projections 221–224 has a further respective indicium thereon which may also be screen printed contemporaneously with the screen printing of the electrodes 65–100. In the present embodiment these further indicia are represented by respective lines 271–274. Thus, the line 271 is located between electrodes 70 and 71, the line 272 between electrodes 79 and 80, the line 273 between electrodes 91 and 92, and the line 274 between electrodes 98 and 99. In place of the lines 271–274 there may be provided respective slits or openings for enabling placement of the assembly 210. Whereas the arrows/legends (or notches) 261–264 provide for the correct placement of the device across the width of the thorax of the body, the lines 271–274 (or slits) provide for the correct placement of the device 210 relative to the height of the body.

When the arrows/legends 261–264 are in register with the relevant portions of the body and the lines 271–274 are in substantially the same notional straight or curved line, correct placement of the device 210 is achieved in which the projections 221–224 will be in substantially parallel spaced-apart relationship. It will also be appreciated that not only is correct placement achieved but also that when the device 210 is placed subsequently on the same body, reproducibility of results is obtained. In other words, the same locations of the cardiac muscle are monitored. Furthermore, having regard to the ability of the projections 221–224 to be moveable relative to each other, the size of the thorax, whether it is an endomorph, ectomorph or mesomorph type, is irrelevant as the arrows/legends 261–264 may be placed on the relevant anatomical locations.

As with the first embodiment, it is preferred during the course of manufacture to provide a removable backing strip (not shown) which would provide a support for the projections 221–224. The assembly can be constructed using techniques and materials known in the art.

In use, the sensor device 210 is offered to the posterior thorax of a body and the various indicia previously described are aligned and placed in the desired locations. The terminal portion 231 is connected as described with respect to the terminal portions 131–134. In particular, the projection 242 is offered to the posterior thorax so that the arrow 262 is placed on the 3rd Thoracic Spinous Process. The remaining projections 221, 223 and 224 are offered so that the legend "LEFT AX" is placed on the left Posterior auxiliary line, the legend "RIGHT AX" is placed on the right posterior auxiliary line and the legend "RIGHT LAT" is placed on the right lateral position of the posterior thorax. The device 210 may be used simultaneously with the assembly of FIG. 1, or by itself.

Figure 3:
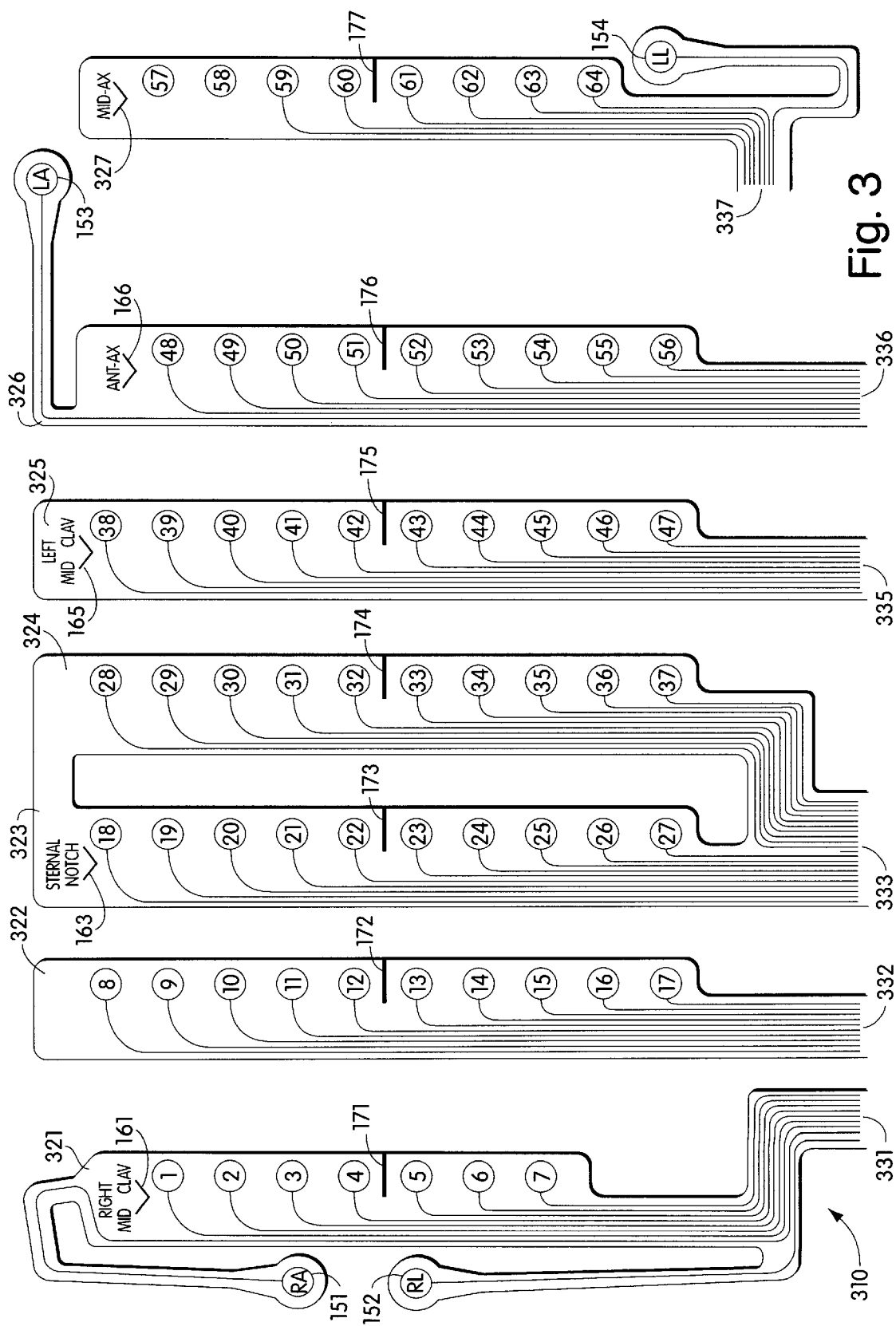
FIG. 3 is a plan view of a third embodiment of an assembly according to the invention.

Reference is now made to FIG. 3 of the drawings. An device 310 is shown which comprises a plurality of finger-like projections 321, 322, 323, 324, 325, 326 and 327. Each of these projections is similar in construction to, and possesses all the features of, corresponding respective projections 121–127 as shown and described with respect to FIG. 1 of the drawings except as follows. In FIG. 1 the projections are joined by a common substrate portion 112 and the electrodes thereon are connected by their leads to one of four terminal portions 131–134. However, in the present embodiment the projections 321, 322, 325, 326 and 317 are separate elements, and each has a respective terminal portion 331, 332, 335, 336 and 337. Only the projections 323 and 324 are joined, and they share a common terminal portion 333. Otherwise, the projections 321–327 function in a manner similar to that of the projections of FIG. 1 of the drawings and the same reference numerals have been used for equivalent features.

It will be appreciated that the sensor device 210 of FIG. 2 of the drawings may also be configured in a similar manner to the sensor device 310 by providing separate projections equivalent to the projections 221–224 each have its own terminal portion similar to the terminal portion 231.

With reference to FIG. 4 of the drawings, there is shown a sensor device 410 similar to the sensor device 310 except as follows. There is provided only five projections 421–425, rather than seven, each bearing a respective arrow or other datum which are labeled respectively "RIGHT AX", "RIGHT MID CLAV", "STERNAL NOTCH ", "LEFT MID CLAV " and "LEFT AX " as indicated. In addition, the total number of electrodes on the projections is 20 rather than 64. Otherwise, the sensor device 410 functions in a manner similar to the device 310.

The invention is not limited by or to the specific embodiments described which can undergo considerable variation without departing from the scope of the invention.

For example, while the particular embodiments described above have sensor devices having 20, 36 and 64 electrodes, with four extension electrodes for attachment to the limbs in the case of an anterior thorax assembly, the device may have up to 300 or more electrodes.

What is claimed is:

1. A sensor device for monitoring bioelectric data from a body comprising:
    a flexible dielectric substrate;
    a plurality of substantially parallel finger-like projections formed integrally from the flexible substrate;
    a plurality of sensors formed on and distributed along the length of each finger-like projection;
    a flexible, electrically conductive network formed on each finger-like projection and respectively connecting each sensor to a terminal portion formed on the flexible substrate; positioning means for positioning the plurality of finger-like projections and therefore sensors on a body in predetermined positions, at a predetermined position on the body; wherein each finger-like projection is spaced laterally from the others of the plurality of finger-like projections by a laterally extending portion of the flexible substrate for adjusting the lateral distance between the substantially parallel finger-like projections by means of bending or folding the laterally extending portion when positioning the sensor device on a body in accordance with the positioning means.

2. The device of claim 1, wherein the sensors are screen-printed on the flexible dielectric substrate.

3. The device of claim 1, wherein the electrically conductive network is screen printed on the flexible substrate.

4. The device of claim 2, wherein the sensors are pregelled using an adhesive hydrogel material.

5. The device of claim 2, wherein the number of sensors is at least 65.

6. The device of claim 1, further comprising at least one extension bearing a respective sensor of the flexible substrate, and wherein the at least one extension is adapted for placement on one of the limbs of the body.

7. The device of claim 6, wherein the number of extensions is 4 and each extension is adapted for placement on a different limb on the body.

8. The device of claim 1, wherein the plurality of sensors and the flexible conductive network are disposed on one side of the flexible substrate, and the other side of the substrate comprises a material adapted to attach the flexible substrate to the body.

9. The device of claim 1, wherein the flexible substrate is adapted for attachment to the anterior thorax of the body.

10. The device of claim 1, wherein the flexible substrate is adapted for attachment to the posterior thorax of the body.

11. The device of claim 1, wherein the flexible substrate is adapted for attachment to the anterior and the posterior thorax of the body and comprises at least 100 sensors in total.

12. The device of claim 1, wherein each of the finger-like projections is joined to each of the other finger-like projections on one end of each by a single section of the flexible substrate to produce a hand-like configuration, and wherein the terminal portion is formed on the single section of the substrate for adaption to connection with cardiac monitoring equipment.

13. The device of claim 1, wherein the positioning means comprises an indicium on each of the finger-like projections to guide in the positioning of the projections on the body.

14. The device of claim 1, wherein the positioning means comprises a first indicium on at least two of the finger-like projections to guide the positioning of the projections across the width of the body.

15. The device of claim 1, wherein the positioning means comprises a second indicium on at least two of the projections to guide in positioning the projections across the height of the body.

16. The device of claim 14, and wherein a second positioning means comprises a second indicium on at least two of the projections to guide in positioning the projections across the height of the body, whereby, when the device is positioned on the torso of the body, the finger-like projections are in a substantially parallel spaced apart relationship to one another.

17. The device of claim 13, wherein the indicium is in the form of printed indications of desired locations of the finger-like projections on the torso of the body.

18. The device of claim 13, wherein the indicium is in the form of printed lines to indicate the relative positioning of the finger-like projections along the length of the torso of the body.

* * * * *